(12) United States Patent
Matsunami et al.

(10) Patent No.: US 7,055,369 B2
(45) Date of Patent: Jun. 6, 2006

(54) GAS DETECTOR HAVING CLOG-RESISTANT INTAKE FILTER AND PROTECTIVE CAP

(75) Inventors: Takanori Matsunami, Obu (JP); Takaaki Takagi, Obu (JP); Koji Yoshikawa, Obu (JP)

(73) Assignee: Aisan Kogyo Kabushiki Kaisha, Aichi-Ken (JP)

( * ) Notice: Subject to any disclaimer, the term of this patent is extended or adjusted under 35 U.S.C. 154(b) by 0 days.

(21) Appl. No.: 10/702,483

(22) Filed: Nov. 7, 2003

(65) Prior Publication Data
US 2004/0093930 A1    May 20, 2004

(30) Foreign Application Priority Data
Nov. 14, 2002   (JP)   ............... 2002-330464

(51) Int. Cl.
 *G01N 7/00*   (2006.01)
(52) U.S. Cl. ............................................. 73/31.01
(58) Field of Classification Search ........... 73/31.07, 73/863.21, 863.23, 863.24, 863.25
See application file for complete search history.

(56) References Cited

U.S. PATENT DOCUMENTS

| | | | |
|---|---|---|---|
| 1,220,037 A * | 3/1917 | Werner et al. | 73/31.07 |
| 4,158,958 A * | 6/1979 | Braun | 73/31.07 |
| 4,745,796 A * | 5/1988 | Abdelrahman et al. | 73/31.07 |
| 5,054,328 A * | 10/1991 | Long et al. | 73/864.81 |
| 6,453,723 B1 * | 9/2002 | Ichikawa et al. | 73/23.2 |
| 6,454,923 B1 | 9/2002 | Dodgson et al. | |
| 6,526,805 B1 * | 3/2003 | Babes-Dornea et al. | 73/19.12 |
| 6,827,232 B1 | 12/2004 | Hara et al. | |
| 2002/0008023 A1 | 1/2002 | Mallory | |
| 2004/0016288 A1 * | 1/2004 | Nikolskaya | 73/31.07 |

FOREIGN PATENT DOCUMENTS

| | | |
|---|---|---|
| JP | 50150392 | 12/1975 |
| JP | 6262958 | 4/1987 |
| JP | 1140162 | 9/1989 |
| JP | 1140162 | 9/1999 |
| JP | 2000249678 | 9/2000 |
| JP | 3213148 | 7/2001 |
| JP | 200271622 | 3/2002 |
| JP | 200271627 | 3/2002 |
| JP | 2002286685 | 10/2002 |
| JP | 2002310970 | 10/2002 |

OTHER PUBLICATIONS http://www.membrana.de/oxygenation/products/celgard.htm.*
www.celgard.com/products/fsmproperties.cfm.*
Japanese Office Action dated Apr. 12, 2005 with English translation.
Japanese Office Action dated Jul. 19, 2005 with English translation.
German Office Action dated Nov. 14, 2005 with English translation.

* cited by examiner

*Primary Examiner*—Michael Cygan
(74) *Attorney, Agent, or Firm*—Stevens, Davis, Miller & Mosher, LLP

(57) ABSTRACT

A gas detector having an intake to let in the gas to be detected and detecting the gas let in through the intake by a gas sensor, in which a porous film is horizontally arranged over the gas intake, in order to prevent the gas permeability of the porous film from being affected by water, oil and/or dust riding on the porous film, wherein a water-repellant and oil-repellant porous film is horizontally provided in a stretched state over the upper end of the intake, and the outside of the outer circumferential edge of the porous film is so structured as to allow liquid on the porous film to fall externally.

4 Claims, 4 Drawing Sheets

RELATED ART

GAS DETECTOR HAVING CLOG-RESISTANT INTAKE FILTER AND PROTECTIVE CAP

FILED OF THE INVENTION

The present invention relates to a gas detector.

DESCRIPTION OF THE RELATED ART

In a gas detector according to the prior art wherein external gas is let in through an intake and its concentration is detected by a gas sensor and electronic components provided within the detector, as shown in FIGS. 8A and 8B, the structure is known that a gas intake 101 is arranged to be open toward above a gas detector 102, the gas intake 101 is provided with a porous film (water-repellant filter) 103 arranged horizontally to ensure gas permeability, waterproofness and dustproofness of the intake 101, and the circumference of the porous film 103 is pinched between internal and external holding members 104 and 105 and the porous film 103 is arranged in a stretched state. For instance, see JP-A-2002-71627, in particular FIG. 1 therein.

In the above-described structure according to the prior art in which the porous film 103 is arranged horizontally and there is the holding member 104 on the upper face of the porous film at the circumference thereof, the presence of the holding member 104 forms a deep concave 106 on the porous film 103. Therefore, if vapor is condensed on the porous film 103 to generate a water drop W1 on its upper face as shown in FIG. 8A, that water drop W1 will be prevented by the holding member 104 around from being drained out of the outer circumference, deposit in the concave 106 and grow to become a water screen W2 as shown in FIG. 8B, thereby giving rise to a problem that the porous film 103 is clogged and its gas permeability is adversely affected.

Further, when dust rises on the porous film 103, since the dust is not discharged out of the outer circumference, it will deposit all over the upper face of the porous film 103 and clog the porous film 103, also thereby, giving rise to the problem of adversely affecting its gas permeability.

SUMMARY OF THE INVENTION

An object of the present invention is to provide a gas detector capable of solving the problem noted above.

In order to solve this problem, according to the invention, there is provided a gas detector which has an intake to let in the gas to be detected and in which the gas let in through the intake is detected by a gas sensor, wherein the intake is formed upward, a porous film having water-repellant and oil-repellant properties is horizontally provided in a stretched state at the upper end of the intake, and the outside of the outer circumferential edge of the porous film is so structured as to enable any liquid on the porous film to fall externally.

In the invention, gas having permeated the porous film enters the intake, and is detected by the gas sensor.

Liquid, which may be water or oil, having condensed on the porous film is caused to form a ball shape on the porous film by the water-repellant and oil-repellant properties of the porous film. As the outside of the outer circumferential edge of the porous film is so structured as to enable liquid on the porous film to fall externally, external forces such as external vibration or acceleration/deceleration working on the gas detector causes this ball-shaped liquid to fall away from the porous film externally. Therefore, the liquid does not deposit in a water-screen form, and accordingly gas permeability is ensured all the time, with reliable detection of gas secured. Also, any dust having flied onto the porous film would fall away from the porous film externally.

In the invention, the upper face of the circumferential wall constituting the intake may be formed as a smooth face, and the outer circumference of the porous film, tightly fastened to the upper face of the circumferential wall.

This configuration, too, provides the same effects and advantages as the foregoing.

Further, in the invention, a projection may be provided on the outer circumference of the top face of the circumferential wall constituting the intake, the porous film being stretched and positioned inside the projection, and the height of the projection being set not too great for the liquid on the porous film to fall outside the porous film.

With this configuration, the projection can serve to position the porous film in fitting the porous film to the circumferential wall in addition to providing the same effects and advantages as the foregoing.

Further, in the invention, the porous film may be formed of PTFE resin.

This configuration also provides the same effects and advantages as the foregoing.

Further, in the invention, a protective cap may be provided over said porous film, with a space being secured to let the external atmosphere flow in over the porous film.

With this configuration, the porous film can be protected from external forces in addition to providing the same effects and advantages as the foregoing.

BRIEF DESCRIPTION OF THE INVENTION

DESCRIPTION OF THE PREFERRED EMBODIMENTS OF THE INVENTION

Preferred modes of implementing the present invention will be described below with reference to embodiments thereof shown in FIG. 1 through FIG. 7.

Figure 1:
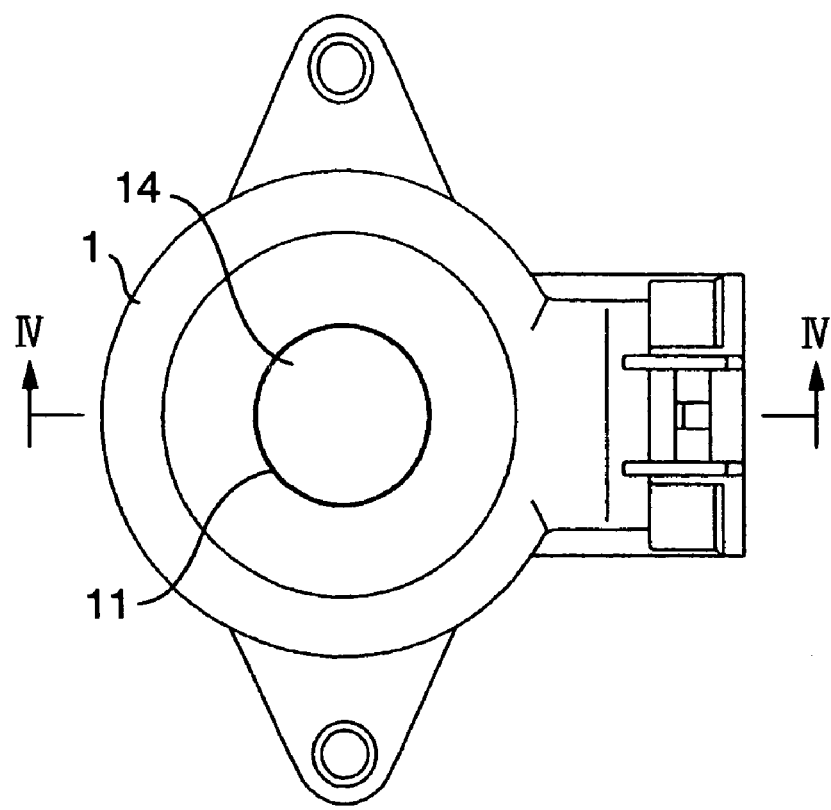
FIG. 1 is a plan view of a gas detector, which is a first embodiment according to the present invention.
Figure 5:
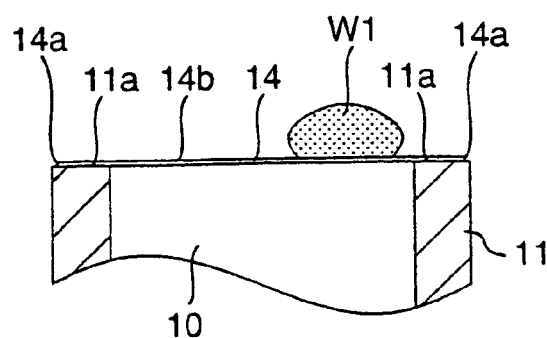
FIG. 5 is an enlarged side section of the porous film portion shown in FIG. 4.

FIG. 1 and FIG. 5 illustrate a first preferred embodiment.

A gas detector according to the invention is usable in a gas leak detector which, in the event of a leak of flammable gas such as carbon monoxide, methane gas, hydrogen gas or LPG, can detect the leaked gas before it takes fire, and the embodiment illustrated here is an example of its application to a gas leak detector.

Figure 2:
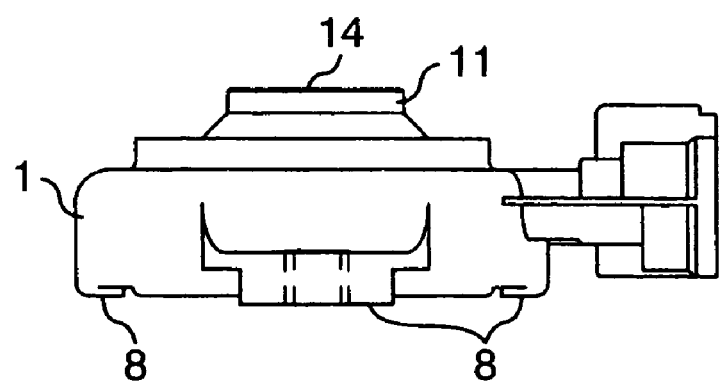
FIG. 2 is a side view of the gas detector shown in FIG. 1.
Figure 3:
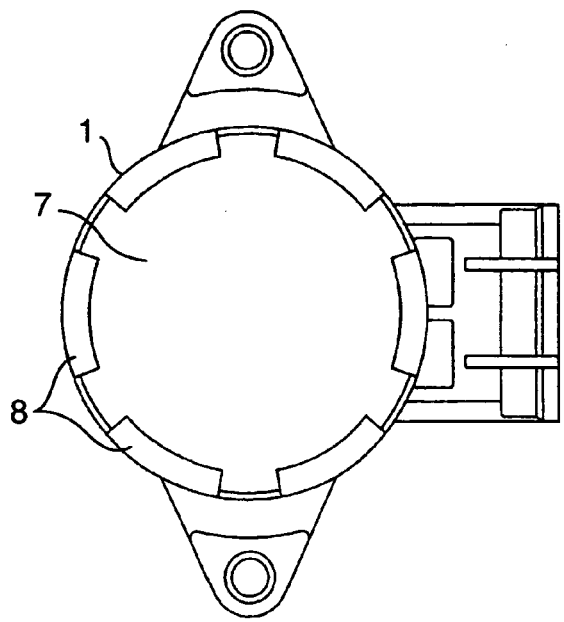
FIG. 3 is a bottom view of the gas detector shown in FIG. 1.
Figure 4:
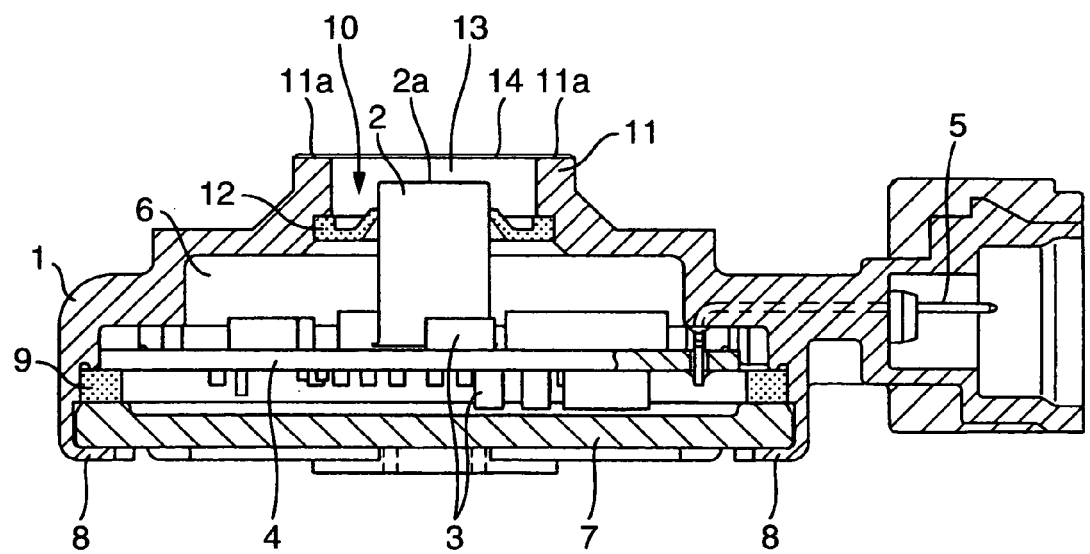
FIG. 4 is an enlarged side section taken along a IV—IV line of the gas detector shown in FIG. 1.

FIG. 1 is a plan view; FIG. 2, a side view; and FIG. 3, a bottom view of the gas detector; FIG. 4 is an enlarged side section taken along a IV—IV line of the gas detector shown in FIG. 1; and FIG. 5 is an enlarged side section of the porous film portion in FIG. 4.

Referring to FIG. 4, a housing 1 is formed of resin, and the housing 1 accommodates a gas sensor 2 and a substrate 4 on which are mounted electronic components 3 connected to the gas sensor 2, and signals from the electronic components 3 indicating the presence or absence of gas are transmitted from a coupling terminal 5 to a prescribed place.

The underside opening of a substrate accommodating chamber 6 accommodating the substrate 4 is blocked by a cover 7, and the cover 7 is caulk-fastened with caulking pieces 8 of the housing 1. Further, the substrate 4 is pressed by the cover 7 with a packing 9.

In the upper part of the housing 1, a cylindrical circumferential wall 11 constituting an intake 10 for letting gas in is formed of the same material as and integrated with the housing 1. The top face 11a of the circumferential wall 11 is formed flat and smooth. The detecting end 2a of the gas sensor 2 is arranged within the intake 10, and the inner circumferential face of a partitioning member 12 fixed tightly to the housing 1 is adhered tightly to the circumference of the body of the gas sensor 2. The detecting end 2a of the gas sensor 2 is positioned in a gas detecting space 13, which is partitioned from the substrate accommodating chamber 6.

The upper part of the gas detecting space 13 is covered by a porous film 14. The porous film 14 is arranged horizontally, and the periphery of the porous film 14 is fastened to the top face 11a of the circumferential wall 11 so as to stretch the porous film 14. The fastening may be accomplished by any appropriate means, such as the use of an adhesive, deposition, or insert molding with the housing 1. The outer circumferential edge 14a of the porous film 14 is free, as shown in FIG. 5, namely no member is provided outside the outer circumferential edge 14a, so that any water, oil and/or dust that may ride on the (top) surface 14b of the porous film 14 can easily drop off sideways.

The porous film 14 does not let dust pass its pores, and repels water and oil, but does allow gas to permeate. For instance a polytetrafluoroethylene (PTFE) film (porous film of PTFE resin), more preferably a PTFE film of 1.0 μm in pore diameter and 200 μm in thickness (available from Nitto Denko Corporation by the product ID number of NTF2131-S06) is used.

The structure described above allows gas diffused from the outer atmosphere to permeate the porous film 14 and flow into the gas detecting space 13. Then, since the gas detecting space 13 is separated from the substrate accommodating chamber 6 by the partitioning member 12, the gas that has flowed into the gas detecting space 13 does not diffuse within the substrate accommodating chamber 6, thereby contributing to quicker detection.

When gas flows into the gas detecting space 13 as stated above, the gas is detected by the gas sensor 2, and gas leak signals are transmitted from the electronic components 3 to prescribed positions.

In liquid, such as water or oil, that has condensed on the porous film 14, by the water-repellant and oil-repellant actions of the porous film 14, without permeating the porous film 14, the angle of contact of the liquid becomes greater on the surface 14b of the porous film 14, resulting in its condensation to a ball-shaped liquid W1 as shown in FIG. 5. This ball-shaped liquid W1 slides on the porous film 14 when the housing 1 of the gas detector vibrates, because the porous film 14 is stretched horizontally and smoothly, and the ball-shaped liquid is discharged down externally from the outer circumferential edge of the porous film 14. Therefore, unlike in the example of the prior art described above, water or oil does not form a screen layer on the porous film to obstruct gas permeability, but the presence or absence of gas can be detected all the time.

For instance, when this gas detector is mounted on a motor vehicle to detect any leak of its fuel, hydrogen gas or LPG, the vibration and acceleration/deceleration during the running of the vehicle causes the ball-like liquid W1 to be discharged.

Also, dust flying onto the porous film 14 is discharged down externally from the outer circumferential edge of the porous film 14 by the vibration of the porous film 14. Therefore, there is no possibility for the porous film 14 to be clogged with dust, deteriorated in gas permeability and obstructed in gas detection.

Figure 6:
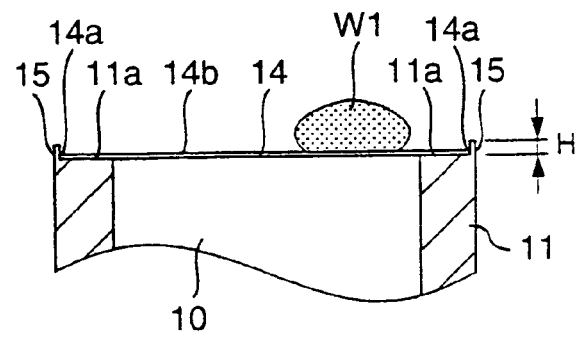
FIG. 6 is an enlarged side section of a porous film portion, which is a second embodiment according to the invention.

FIG. 6 shows a second embodiment according to the present invention.

In this second embodiment, a positioning projection 15 which comes into contact with the outer circumferential edge 14a of the porous film 14 is formed integrally with the circumferential wall 11 on the top face 11a of the circumferential wall 11 of the housing 1, to which the porous film 14 is to be fitted, in the first embodiment described above. This projection 15 may be either formed in a ring shape all around in the circumferential direction or formed partially in the circumferential direction.

The height H of the projection 15 should not be too great for the ball-like liquid W1 to be caused to ride over the projection 15 by vibration, such as what was mentioned above, and fall outside. For instance, the height H is set smaller than the diameter size of the ball-like liquid W1, and preferably about 0.1 mm.

The structure of the second embodiment is the same in all other respects as that of the first embodiment described above.

In this second embodiment, the projection 15 performs a positioning role in fitting the porous film 14 to the circumferential wall 11 of the housing 1, thereby facilitating fitting the porous film 14 and enhancing the accuracy of the fitting position.

Figure 7:
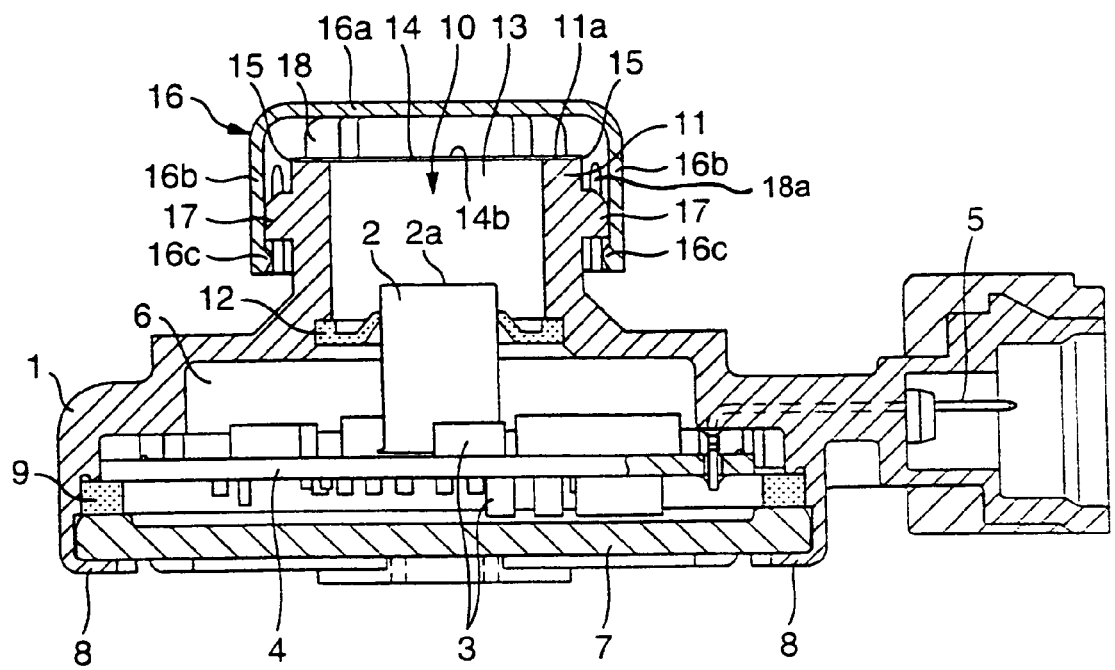
FIG. 7 is a side section of a gas detector, which is a third embodiment according to the invention.
Figure 8A:
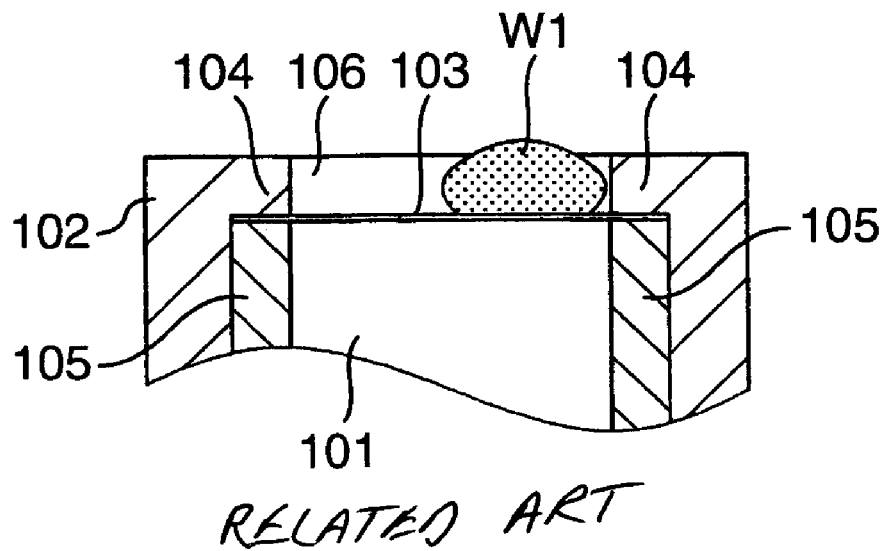
FIGS. 8A and 8B are side sections of the essential part of a structure according to the prior art, FIG. 8A showing a state in which a ball-shaped liquid is stuck and FIG. 8B, a state in which the ball-shaped liquid in FIG. 8A has become a water screen.
Figure 8B:
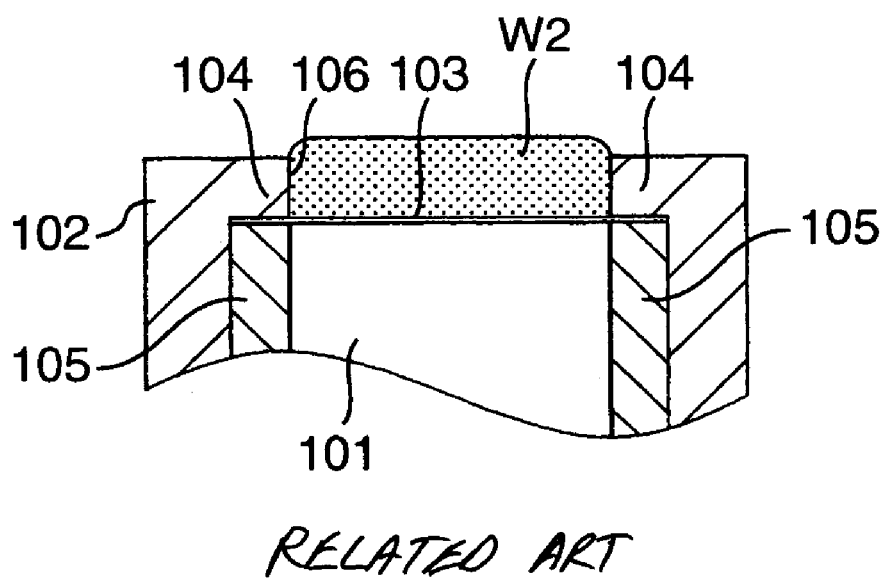

FIG. 7 shows a third preferred embodiment according to the present invention.

In this third embodiment, the above-described structure of the second embodiment having the projection 15 is provided with a protective cap 16 over the porous film 14.

Thus, there is used the protective cap 16 molded of resin integrally with a protective plate 16a slightly greater in diameter than the porous film 14, legs 16b partially suspending from the outer circumference of the protective plate 16a, and engaging claws 16c formed at lower ends of the legs 16b. The legs 16b of the protective cap 16 are snap-fitted to engaging portions 17 formed on the outer face of the circumferential wall 11, so that the protective plate 16a covers over the surface 14b of the porous film 14 in a state that the protective plate 16a is separated upward from the surface 14b of the porous film 14.

Since the structure of this embodiment is the same in all other respects than the first embodiment described above, the same elements as their counterparts in the first embodiment are denoted by the same signs, and their description is dispensed with.

In this third embodiment, gas passes a space 18 between the porous film 14 and the Drotective Diate 16*a* and a space 18*a* between the legs 16*b* of the protective cap 16 and the housing 1 to ensure unobstructed detection of the gas, and the protective plate 16*a* of the protective cap 16 can protect the porous film 14 from external forces.

Incidentally, the protective cap 16 may as well be added to the structure of the first embodiment in the same way as described above.

As hitherto described, since the invention enables liquid, such as water or oil, riding on or dust having flied onto the upper face of the porous film to be discharged away from the porous film by the vibration of the gas detector, it is possible to prevent the whole face of the porous film from being clogged with water, oil and/or dust, which would make it impossible to detect gas, and to ensure gas permeability all the time and successful detection of gas.

Further, by providing the projection on the outer circumference of the upper face of the circumferential wall of the intake, the projection can serve to position the porous film, to facilitate fitting of the porous film and to enhance the accuracy of the porous film, in addition to realizing the above-stated advantage.

By providing the protective cap over the porous film, the porous film can be protected from external forces in addition to realizing the above-stated advantage.

What is claimed is:

1. A gas detector used in the atmosphere which includes a housing having an intake to let in the gas to be detected and in which the gas let in through the intake is detected by a gas sensor, wherein:

said intake is formed upward in said housing, a porous film having waterrepellant and oil-repellant properties is stretched horizontally at an upper end of the intake, a protective cap is provided on said housing, which has a protective plate covering over a surface of said porous film in a state that the protective plate is separated upward from the surface of the porous film and leg portions suspending from an outer peripheral surface of the protective plate, and a gas passage is defined by said housing and said protective cap, which is open so that gas enters at extreme ends of said leg portions which are not circumferentially sealed to the housing and is bent at an upper portion in a horizontal direction, with a space defined between the porous film and said protective plate being secured to let the external atmosphere flow in over the porous film through said gas passage.

2. A gas detector according to claim 1, wherein said porous film is formed of PTFE resin.

3. A gas detector according to claim 1, wherein said gas sensor is provided in said housing so as to arrange a gas detecting end of said gas sensor within said intake, and an inner circumferential face of a partitioning member fixed tightly to said housing is adhered tightly to a circumference of a body of the gas sensor, and said detecting end of said gas sensor is positioned in a gas detecting space.

4. A gas detector according to claim 3, wherein said porous film is formed of PTFE resin.

* * * * *